(12) United States Patent
Kramer et al.

(10) Patent No.: US 10,549,024 B1
(45) Date of Patent: Feb. 4, 2020

(54) FACILITATING PERCUTANEOUS INTRAVASCULAR ACCESS FOR CATHETERS ACCOMMODATING HIGH VOLUMETRIC FLOW RATES

(71) Applicants: Radu Kramer, Woodcliff Lake, NJ (US); Arthur Jacob, Hackensack, NJ (US)

(72) Inventors: Radu Kramer, Woodcliff Lake, NJ (US); Arthur Jacob, Hackensack, NJ (US)

(*) Notice: Subject to any disclaimer, the term of this patent is extended or adjusted under 35 U.S.C. 154(b) by 2 days.

(21) Appl. No.: 16/241,146

(22) Filed: Jan. 7, 2019

(51) Int. Cl.
*A61M 1/36* (2006.01)
*A61M 25/00* (2006.01)
*A61M 5/158* (2006.01)

(52) U.S. Cl.
CPC ........ *A61M 1/3661* (2014.02); *A61M 25/003* (2013.01); *A61M 5/1582* (2013.01); *A61M 2005/1588* (2013.01); *A61M 2025/0031* (2013.01)

(58) Field of Classification Search
CPC .. A61M 2025/0024; A61M 2025/0025; A61M 25/0032; A61M 2025/0034; A61M 25/0074; A61M 25/0144; A61M 25/005; A61M 25/003; A61M 25/0067; A61M 25/008; A61M 2025/0035
See application file for complete search history.

(56) References Cited

U.S. PATENT DOCUMENTS

| | | | |
|---|---|---|---|
| 4,073,297 A | 2/1978 | Kopp | |
| 4,675,004 A | 6/1987 | Hadford et al. | |
| 4,770,652 A | 9/1988 | Mahurkar | |
| 4,776,841 A | 10/1988 | Catalano | |
| 4,842,582 A | 6/1989 | Mahurkar | |
| 4,897,079 A | 1/1990 | Zaleski et al. | |
| 5,382,238 A * | 1/1995 | Abrahamson | A61M 25/0102 600/434 |
| 5,807,311 A * | 9/1998 | Palestrant | A61M 25/003 604/28 |
| 6,295,990 B1 * | 10/2001 | Lewis | A61B 17/22 128/898 |
| 8,308,674 B1 | 11/2012 | Montroni | |
| 8,512,290 B2 | 8/2013 | Rioux et al. | |
| 9,174,008 B1 | 11/2015 | Kramer | |

(Continued)

*Primary Examiner* — Nathan R Price
*Assistant Examiner* — William R Frehe
(74) *Attorney, Agent, or Firm* — Arthur Jacob

(57) ABSTRACT

A catheter and a method facilitate insertion into a blood vessel by providing a tubular wall section with a lumen having a longitudinally extending first volume and a second volume extending side-by-side and contiguous with the first volume. A sector of the tubular wall section is extended side-by-side and contiguous with the second volume of the lumen and is constructed of a material enabling the sector to be collapsed diametrically and nested within the first volume so that the section is provided with limited diametric dimensions. Upon insertion of the section into the blood vessel, the sector is expanded to extend diametrically outside the first volume, thereby rendering the section configured with expanded diametric dimensions and the lumen with a total cross-sectional area for accommodating a desired relatively high volumetric flow rate of fluid through the catheter.

25 Claims, 5 Drawing Sheets

(56) References Cited

U.S. PATENT DOCUMENTS

| | | | |
|---|---|---|---|
| 9,724,075 B2 | 8/2017 | Kramer et al. | |
| 2006/0235458 A1* | 10/2006 | Belson | A61M 25/0032 606/191 |
| 2008/0243081 A1* | 10/2008 | Nance | A61B 17/3439 604/164.03 |
| 2009/0187118 A1* | 7/2009 | Kim | A61B 5/150022 600/583 |
| 2013/0211324 A1* | 8/2013 | Voss | A61B 17/0057 604/104 |
| 2014/0236122 A1* | 8/2014 | Anderson | A61M 25/005 604/523 |
| 2015/0238178 A1* | 8/2015 | Carroux | A61B 17/0218 600/208 |
| 2016/0144097 A1 | 5/2016 | Turk et al. | |
| 2017/0281344 A1* | 10/2017 | Costello | A61F 2/2427 |

* cited by examiner

FACILITATING PERCUTANEOUS INTRAVASCULAR ACCESS FOR CATHETERS ACCOMMODATING HIGH VOLUMETRIC FLOW RATES

The present invention relates generally to attaining percutaneous intravascular access for catheters that accommodate a relatively high volumetric flow rate of fluid conducted through such catheters and pertains, more specifically, to catheters and methods that enable insertion of a catheter having minimally invasive, limited diametric dimensions during insertion into a blood vessel and which are reconfigured, subsequent to insertion, with expanded diametric dimensions for accommodating a desired, high volumetric rate of flow of fluid through the catheter.

A very wide variety of currently-practiced medical procedures require intravascular access, typically for the establishment of a fluid flow through a needle or a catheter introduced percutaneously into a blood vessel, or a graft, either for administering or withdrawing fluids. For example, a patient undergoing hemodialysis will require, over time, multiple procedures during which hemodialysis needles or catheters are introduced, percutaneously, to gain vascular access. Ordinarily, a hemodialysis procedure is conducted with two needles or catheters, a first needle or catheter being inserted into a blood vessel at a first site for withdrawing blood, while a second needle or catheter is inserted at a second site for returning blood to the blood vessel, requiring a relatively large opening at each insertion site, resulting in patient discomfort, longer healing times, and an increased risk of infection. While dual-flow needles and catheters have been suggested in order to enable insertion at a single site to accommodate both withdrawal and return of blood, such dual-flow needles and catheters are constructed in larger diameters so as to accommodate a requisite high volumetric flow rate of blood, requiring a concomitant larger opening at the single insertion site, with the drawbacks associated with such larger openings, as set forth above.

The present invention provides catheters and methods for accomplishing percutaneous intravascular access while avoiding the drawbacks outlined above. As such, the present invention attains several objects and advantages, some of which are summarized as follows: Enables minimally invasive percutaneous intravascular access for establishing a requisite relatively high volumetric flow rate of fluid into or out of an accessed blood vessel, while militating against the consequences of a larger opening at the access site; accomplishes a requisite high volumetric flow rate through insertion of a relatively small diameter, flexibly comfortable intravascular access tubular member, while avoiding a larger access opening at the insertion site; eliminates the need for more than one access site in a hemodialysis procedure, while reducing the size of the access opening at the single access site; reduces the size of an access opening at an insertion site, and an incursion at a blood vessel associated with the access site, without compromising a desired high volumetric rate of blood flow; increases the accuracy of placement of an inserted tubular member in attaining intravascular access; improves patient comfort and satisfaction; avoids leakage at an insertion site, with a concomitant reduction in blood loss and the risk of spreading blood-born infectious diseases from a patient to attending medical personnel, as well as others; enhances and accelerates healing at the insertion site; reduces the risk of infection; facilitates an intravascular access procedure for added effectiveness with increased ease.

The above objects and advantages, as well as further objects and advantages, are attained by the present invention which may be described briefly as a hemodialysis catheter having a construction for facilitating percutaneous intravascular access, the catheter including a first lumen and a second lumen, the first lumen having a first fluid passage of first predetermined cross-sectional area for accommodating, during the conduct of hemodialysis wherein the catheter is positioned within a blood vessel, a prescribed volumetric flow rate as an arterial flow rate of blood being withdrawn from the blood vessel, while the second lumen has a second fluid passage of second predetermined cross-sectional area corresponding to the first predetermined cross-sectional area for accommodating the prescribed volumetric flow rate as a venous flow rate of blood being returned to the blood vessel, the catheter comprising: a tubular wall having a distal terminal end and a section of limited diametric dimensions for facilitating insertion of the section into the blood vessel, the section extending longitudinally between a proximal end and a distal end juxtaposed with the distal terminal end of the tubular wall, the section including a proximal segment and a distal segment, the proximal segment extending from the proximal end of the section to a distal end at the distal segment, and the distal segment extending from the distal end of the proximal segment to the distal terminal end of the tubular wall; the first lumen extending longitudinally within the proximal segment, with the first fluid passage extending from an entrance orifice juxtaposed with the distal end of the proximal segment to an exit juxtaposed with the proximal end of the section; the second lumen extending longitudinally through the section, from the proximal end of the section to the distal terminal end of the tubular wall, the second fluid passage including a first volume having a first cross-sectional area and a second volume having a second cross-sectional area, the second volume extending side-by-side and contiguous with the first volume; a septum separating the first lumen from the second lumen; the section of the tubular wall including a wall sector having a length extending longitudinally substantially from the proximal end of the section to the distal terminal end of the tubular wall, the wall sector extending side-by-side and contiguous with the second volume of the second fluid passage, with the wall sector bounding the second cross-sectional area; and the wall sector being constructed of a material enabling the wall sector to be collapsed diametrically into a substantially collapsed configuration and to be expanded diametrically between the substantially collapsed configuration, wherein the wall sector is configured and dimensioned for nesting within the first volume of the second fluid passage of the section of the tubular wall, and an expanded configuration wherein the wall sector is extended diametrically outside the first volume of the second fluid passage, thereby supplementing the first volume of first cross-sectional area with the second volume of second cross-sectional area to establish, within the second lumen, the second fluid passage of second predetermined cross-sectional area corresponding to the predetermined cross-sectional area of the first lumen; whereby, with the wall sector in the substantially collapsed configuration and nested within the first volume of the second fluid passage, the section is configured with the limited diametric dimensions for facilitating insertion of the segment into the blood vessel and, upon being positioned within the blood vessel during hemodialysis, the section is reconfigured with the wall sector expanded into the expanded configuration, placed diametrically, outside the first volume of the second fluid passage, thereby rendering the section configured with expanded diametric dimensions and providing the second lumen with the second fluid passage of second predetermined cross-sectional area, for accommodating the venous flow rate of blood being returned to the blood vessel, while the arterial flow rate of blood being withdrawn from the blood vessel is accommodated by the first fluid passage of first predetermined cross-sectional area of the first lumen.

In addition, the present invention includes a catheter having a construction for facilitating percutaneous intravascular access, the construction providing the catheter with a lumen having a fluid passage of predetermined cross-sectional area for accommodating, upon insertion into a blood vessel, a prescribed volumetric flow rate of fluid through the catheter, the catheter comprising: a tubular wall having a distal terminal end and a section of limited diametric dimensions for facilitating insertion of the section into the blood vessel, the section extending longitudinally between a proximal end and the distal terminal end of the tubular wall; the lumen extending longitudinally through the section, from the proximal end of the section to the distal terminal end of the section, the fluid passage including a first volume having a first cross-sectional area, and a second volume having a second cross-sectional area, the second volume extending side-by-side and contiguous with the first volume; the section of the tubular wall including a wall sector having a length extending longitudinally substantially from the proximal end of the section to the distal terminal end of the tubular wall, the wall sector extending side-by-side and contiguous with the second volume of the fluid passage, with the wall sector bounding the second cross-sectional area; and the wall sector being constructed of a material enabling the wall sector to be collapsed diametrically into a substantially collapsed configuration and to be expanded diametrically between the substantially collapsed configuration, wherein the wall sector is configured and dimensioned for nesting within the first volume of the fluid passage, and an expanded configuration wherein the wall sector is extended diametrically outside the first volume, thereby supplementing the first volume of first cross-sectional area with the second volume of second cross-sectional area to establish, within the section, the fluid passage of predetermined cross-sectional area; whereby, with the wall sector in the substantially collapsed configuration and nested within the first volume, the section is configured with the limited diametric dimensions for facilitating insertion of the section into the blood vessel and, upon being positioned within the blood vessel, the section is reconfigured with the wall sector expanded into the diametrically expanded configuration, placed diametrically, outside the first volume, thereby rendering the section configured with expanded diametric dimensions and providing the lumen with the fluid passage of predetermined cross-sectional area for accommodating the prescribed volumetric flow rate of fluid through the catheter.

Further, the present invention provides a method for facilitating percutaneous intravascular access by a hemodialysis catheter, the catheter including a first lumen and a second lumen, the first lumen having a first fluid passage of first predetermined cross-sectional area for accommodating, during the conduct of a hemodialysis procedure wherein the catheter is positioned within a blood vessel, a prescribed volumetric flow rate as an arterial flow rate of blood being withdrawn from the blood vessel, while the second lumen has a second fluid passage of second predetermined cross-sectional area corresponding to the first predetermined cross-sectional area for accommodating the prescribed volumetric flow rate as a venous flow rate of blood being returned to the blood vessel, the method comprising: providing the catheter with a tubular wall having a distal terminal end and a section of limited diametric dimensions for facilitating insertion of the section into the blood vessel; extending the section longitudinally between a proximal end and a distal end juxtaposed with the distal terminal end of the tubular wall; including in the section a proximal segment and a distal segment, with the proximal segment extending from the proximal end of the section to a distal end at the distal segment, and the distal segment extending from the distal end of the proximal segment to the distal terminal end of the tubular wall; extending the first lumen longitudinally within the proximal segment, with the first fluid passage extending from an entrance orifice juxtaposed with the distal end of the proximal segment to an exit juxtaposed with the proximal end of the section; extending the second lumen longitudinally through the section, from the proximal end of the section to the distal terminal end of the tubular wall; including in the second fluid passage a first volume having a first cross-sectional area and a second volume having a second cross-sectional area, the second volume extending side-by-side and contiguous with the first volume; separating the first lumen from the second lumen; including in the section of the tubular wall a wall sector having a length extending longitudinally substantially from the proximal end of the section to the distal terminal end of the tubular wall, the wall sector extending side-by-side and contiguous with the second volume of the second fluid passage, with the wall sector bounding the second cross-sectional area; and constructing the wall sector of a material enabling the wall sector to be collapsed diametrically into a substantially collapsed configuration and to be expanded diametrically between the substantially collapsed configuration, wherein the wall sector is configured and dimensioned for nesting within the first volume of the second fluid passage of the section of the tubular wall, and an expanded configuration wherein the wall sector is to extend diametrically outside the first volume of the second fluid passage, thereby supplementing the first volume of first cross-sectional area with the second volume of second cross-sectional area to establish, within the second lumen, the second fluid passage of second predetermined cross-sectional area corresponding to the predetermined cross-sectional area of the first lumen; whereby, with the wall sector in the substantially collapsed configuration and nested within the first volume of the second fluid passage, the section is configured with the limited diametric dimensions for facilitating insertion of the segment into the blood vessel and, upon being positioned within the blood vessel during hemodialysis, the section is reconfigured with the wall sector expanded into the expanded configuration, placed diametrically outside the first volume of the second fluid passage, thereby rendering the section configured with expanded diametric dimensions and providing the second lumen with the second fluid passage of second predetermined cross-sectional area, for accommodating the venous flow rate of blood being returned to the blood vessel, while the arterial flow rate of blood being withdrawn from the blood vessel is accommodated by the first fluid passage of first predetermined cross-sectional area of the first lumen.

Still further, the present invention includes a method for facilitating percutaneous intravascular access by a catheter, the method comprising: providing the catheter with a tubular wall having a distal terminal end and a section of limited diametric dimensions; extending the section longitudinally between a proximal end and the distal terminal end of the tubular wall; extending a lumen longitudinally through the section, from the proximal end of the section to the distal terminal end of the section; providing the lumen with a fluid passage including a first volume having a first cross-sectional area, and a second volume having a second cross-sectional area, with the second volume extending side-by-side and contiguous with the first volume; including in the section of the tubular wall, a wall sector having a length extending longitudinally substantially from the proximal end of the section to the distal terminal end of the tubular wall, with the wall sector extending side-by-side and contiguous with the second volume of the fluid passage, with the wall sector bounding the second cross-sectional area; and constructing the wall sector of a material enabling the wall sector to be collapsed diametrically into a substantially collapsed configuration and to be expanded diametrically between the substantially collapsed configuration, wherein the wall sector is configured and dimensioned for nesting within the first volume of the fluid passage, and an expanded configuration wherein the wall sector is to extend diametrically outside the first volume, thereby supplementing the first volume of first cross-sectional area with the second volume of second cross-sectional area to establish, within the section, the fluid passage of predetermined cross-sectional area; whereby, with the wall sector in the substantially collapsed configuration and nested within the first volume, the section is configured with the limited diametric dimensions for facilitating insertion of the section into a blood vessel and, upon being positioned within the blood vessel, the section is reconfigured with the wall sector expanded into the expanded configuration, placed diametrically outside the first volume, thereby rendering the section configured with expanded diametric dimensions and providing the lumen with the fluid passage of predetermined cross-sectional area for accommodating the prescribed volumetric flow rate of fluid through the catheter.

The invention will be understood more fully, while still further objects and advantages will become apparent, in the following detailed description of preferred embodiments of the invention illustrated in the accompanying drawing, in which.

Figure 1:
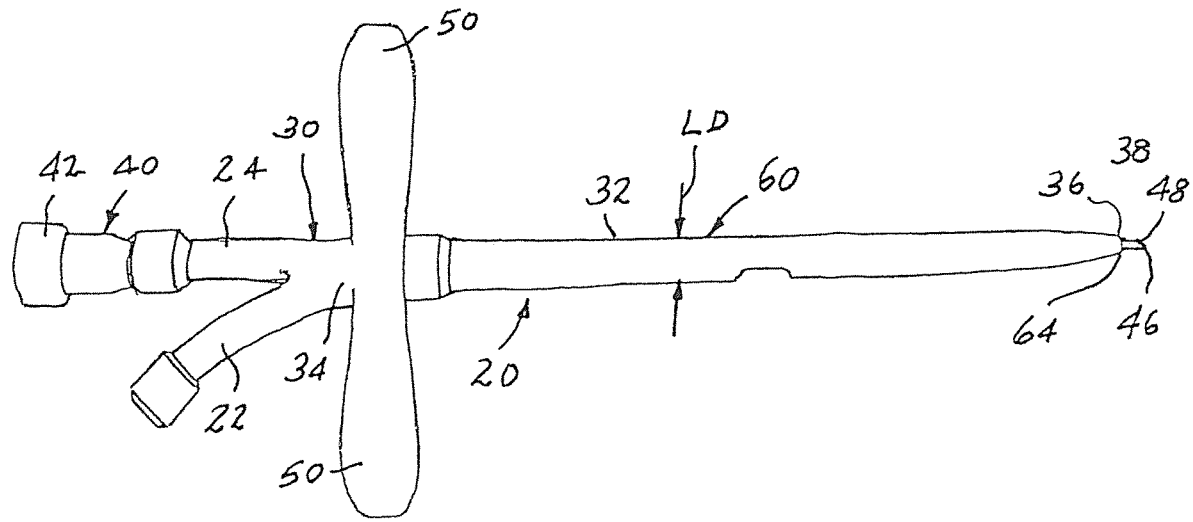
FIG. 1 is a plan view of a hemodialysis catheter constructed in accordance with the present invention.
Figure 2:
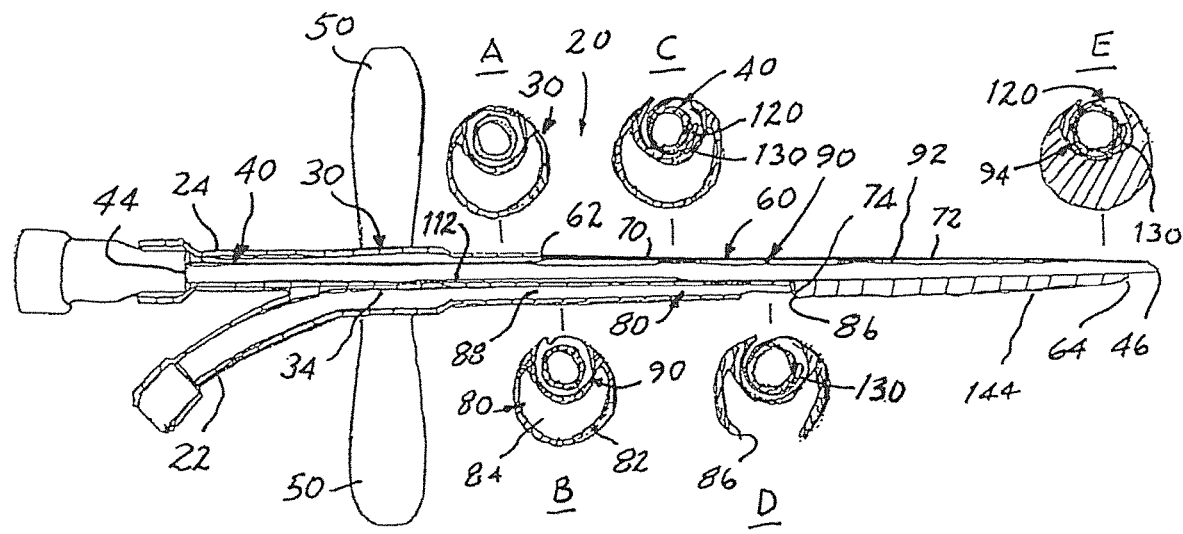
FIG. 2 is a somewhat diagrammatic view showing a longitudinal cross-section of the hemodialysis catheter of FIG. 1, with supplemental transverse cross-sectional views A, B, C, D, and E illustrating structural details.
Figure 3:
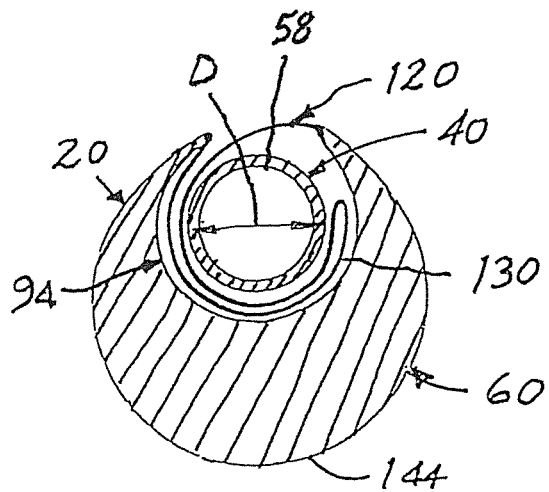
FIG. 3 is an enlarged version of cross-sectional view E of FIG. 2.

Referring now to the drawing, and especially to FIGS. 1 through 3 thereof, a hemodialysis catheter constructed in accordance with the present invention is shown at 20 and is seen to be a dual-flow catheter that includes an arterial branch 22 and a venous branch 24, which branches 22 and 24 merge into a single tubular member 30 having a tubular wall 32 extending longitudinally from a proximal portion 34 of the tubular member 30, where the branches 22 and 24 merge, to a distal terminal end 36 at a distal tip 38 of the tubular member 30.

In preparation for insertion of catheter 20 in connection with the conduct of a hemodialysis procedure, an insertion needle 40 is placed within tubular member 30, as shown in FIGS. 1 through 3, the needle 40 including a handle 42 at the proximal end 44 of the needle 40, a piercing point 46 at the distal end 48 of the needle 40, with the piercing point 46 juxtaposed with the distal tip 38 of the tubular member 30, and a given diameter D. A pair of wings 50 extend radially outwardly from the tubular member 30, adjacent the merged branches 22 and 24, at proximal portion 34 of tubular member 30, and provide finger grips for manipulating catheter 20 during insertion into and removal from a blood vessel at an insertion site, as illustrated in phantom in FIGS. 4 and 5, where catheter 20 is seen inserted into a blood vessel 54 at an insertion site 56 as described more fully below in connection with FIGS. 4 and 5. Insertion needle 40 includes a central passage 58 for confirming the insertion, in the conventional manner.

The construction of catheter 20 provides a dual-flow function enabling catheter 20 to be employed in a hemodialysis procedure as a single catheter for accommodating both an arterial flow at a requisite prescribed volumetric flow rate of blood being withdrawn from a blood vessel, and a venous flow of blood being returned to the blood vessel at the same requisite prescribed volumetric flow rate. In order to accomplish the accommodation of the requisite relatively high prescribed volumetric flow rate of blood into and out of a blood vessel, catheter 20 must be provided with a first lumen having a first fluid passage of first predetermined cross-sectional area for accommodating, during the conduct of the hemodialysis procedure wherein catheter 20 is positioned within a blood vessel at an insertion site, as illustrated by blood vessel 54 at insertion site 56, the requisite prescribed volumetric flow rate as an arterial flow rate of blood being withdrawn from the blood vessel, and a second lumen having a second fluid passage of second predetermined cross-sectional area corresponding to the first predetermined cross-sectional area for accommodating the same requisite prescribed volumetric flow rate, as a venous flow rate of blood being returned to the blood vessel. Thus, catheter 20 must include first and second lumens which together provide a total cross-sectional area comprised of both the first predetermined cross-sectional area and the second predetermined cross-sectional area in order to accommodate the requisite prescribed volumetric flow rate of blood into and out of the blood vessel. In order to accomplish a minimally invasive insertion of catheter 20 at a selected insertion site, catheter 20 is provided with limited diametric dimensions during insertion and a construction which is reconfigured, subsequent to insertion, with expanded diametric dimensions for establishing the total cross-sectional area necessary to accommodate the requisite relatively high prescribed volumetric flow rate of blood through both the first and second lumens during the hemodialysis procedure.

Accordingly, tubular wall 32 includes a section 60 of limited diametric dimensions LD for facilitating insertion of the section 60 into the blood vessel 54 at insertion site 56, section 60 extending longitudinally between a proximal end 62 and a distal end 64 juxtaposed with the distal terminal end 36 of tubular wall 32. Section 60 includes a proximal segment 70 and a distal segment 72, the proximal segment 70 extending from the proximal end 62 of the section 60 to a distal end 74 where the proximal segment 70 joins the distal segment 72. The distal segment 72 extends from the distal end 74 of the proximal segment 70 to the distal terminal end 36 of the tubular wall 32. A first lumen 80 extends longitudinally within the proximal segment 70, providing a first fluid passage 82 having a first predetermined cross-sectional area 84 extending from an entrance orifice 86 juxtaposed with the distal end 74 of the proximal segment 70 to an exit 88 juxtaposed with the proximal end 62 of the section 60. A second lumen 90 extends longitudinally through both the proximal segment 70 and the distal segment 72 of the section 60, from the proximal end 62 of the section 60 to the distal terminal end 36 of the tubular wall 32. A second fluid passage 92 within second lumen 90 includes a first volume 94 having a first cross-sectional area 96 and a second volume 100 having a second cross-sectional area 110, the second volume 100 extending side-by-side and contiguous with the first volume 94. A septum 112 separates the first lumen 80 from the second lumen 90.

Figure 6:
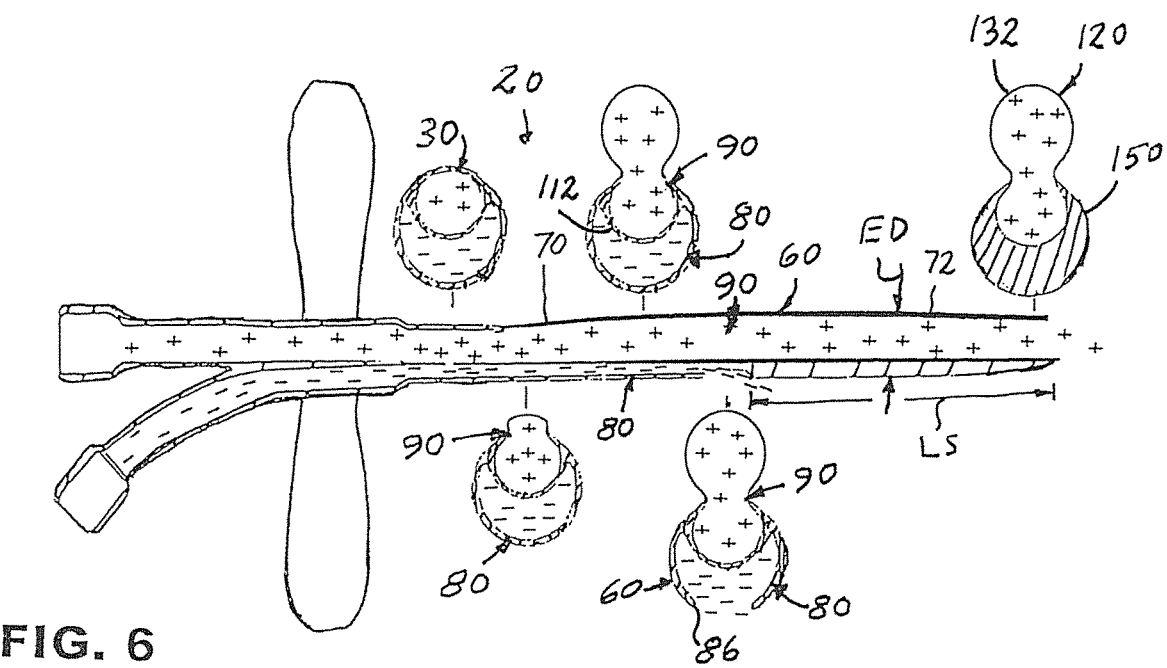
FIG. 6 is a somewhat diagrammatic view similar to FIG. 2 and showing the hemodialysis catheter reconfigured and operating during the stage of operation depicted in FIG. 5, with cross-sectional views A, B, C, D and E reconfigured accordingly.
Figure 7:
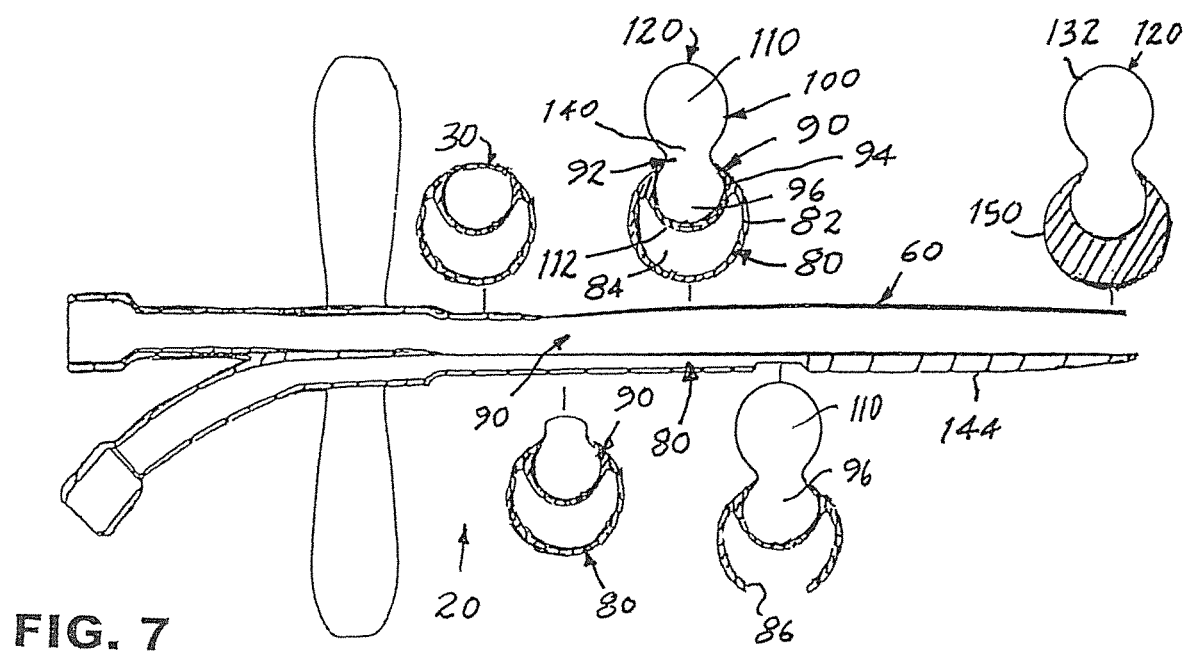
FIG. 7 is a somewhat diagrammatic view similar to FIG. 6, and illustrating the hemodialysis catheter itself in the reconfigured configuration.

The section 60 of the tubular wall 32 is provided with a wall sector 120 having a length extending longitudinally substantially from the proximal end 62 of the section 60 to the distal terminal end 36 of the tubular wall 32, the wall sector 120 extending side-by-side and contiguous with the second volume 100 of the second fluid passage 92, with the wall sector 120 bounding the second cross-sectional area 110. The wall sector 120 is constructed of a material enabling the wall sector 120 to be collapsed diametrically into a substantially collapsed configuration 130, as seen in FIG. 2 at cross-sectional views B, C, D and E, and in FIG. 3, and to be expanded diametrically between the substantially collapsed configuration 130, wherein the wall sector 120 is configured and dimensioned for nesting within the first volume 94 of the second fluid passage 92 of the section 60 of the tubular wall 32, as seen in FIG. 2 at cross-sectional views B, C, D, and E, and in FIG. 3, and an expanded configuration 132, wherein the wall sector 120 is extended diametrically outside the first volume 94 of the second fluid passage 92, as seen in FIGS. 6 and 7, thereby supplementing the first volume 94 having the first cross-sectional area 96 with the second volume 100 having second cross-sectional area 110 to establish, within the second lumen 90, the second fluid passage 92 with a second predetermined cross-sectional area 140 corresponding to the first predetermined cross-sectional area 84 of the first lumen 80. Thus, with the wall sector 120 in the substantially collapsed configuration 130, and nested within the first volume 94 of the second fluid passage 92, as seen in FIGS. 2 and 3, the section 60 is configured with the limited diametric dimensions LD for facilitating insertion of the section 60 into the blood vessel 54. Insertion is further facilitated by the provision of a reinforcing subsection 144 extending longitudinally along the distal segment 72 of section 60, diametrically opposite the wall sector 120, between the entrance orifice 86 and the distal terminal end 36 of the tubular wall 32, with the reinforcing subsection 144 tapered toward the distal terminal end 36.

Figure 4:
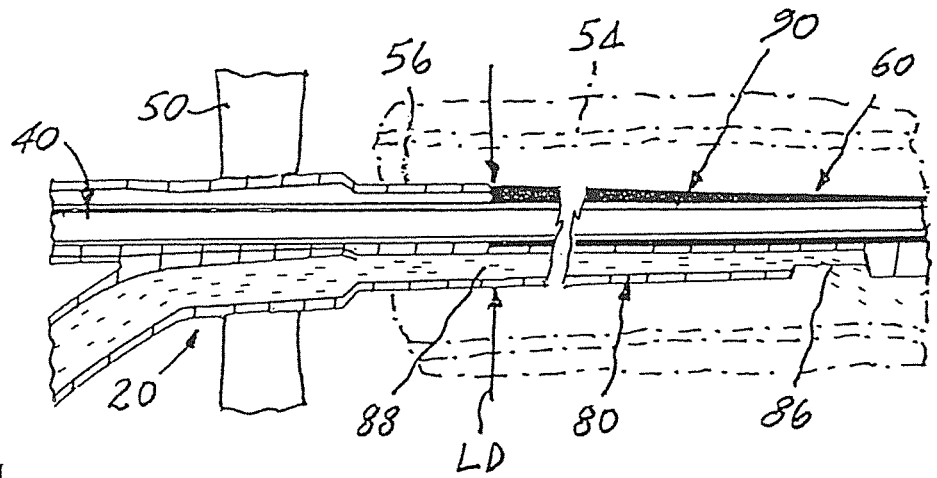
FIG. 4 is an enlarged fragmentary longitudinal cross-sectional view showing a stage of operation of the hemodialysis catheter, subsequent to insertion.
Figure 5:
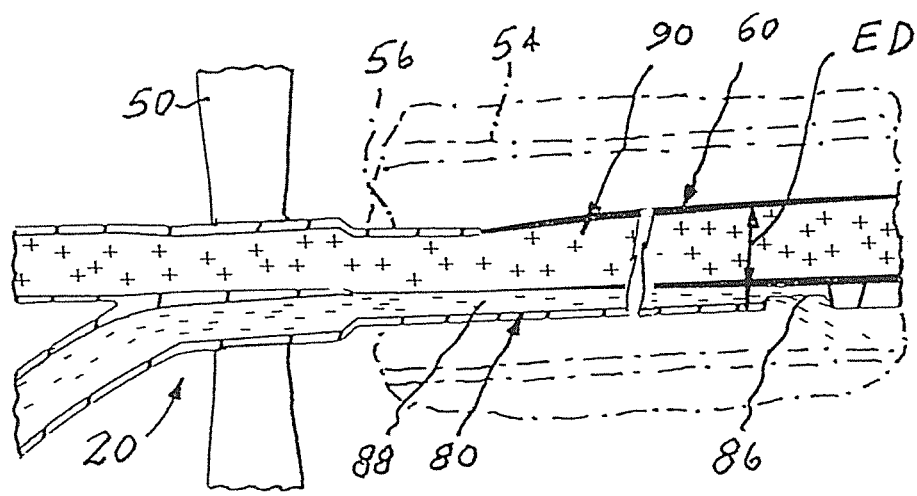
FIG. 5 is an enlarged fragmentary longitudinal cross-sectional view similar to FIG. 4 and showing a further stage of operation of the hemodialysis catheter.
Figure 8:
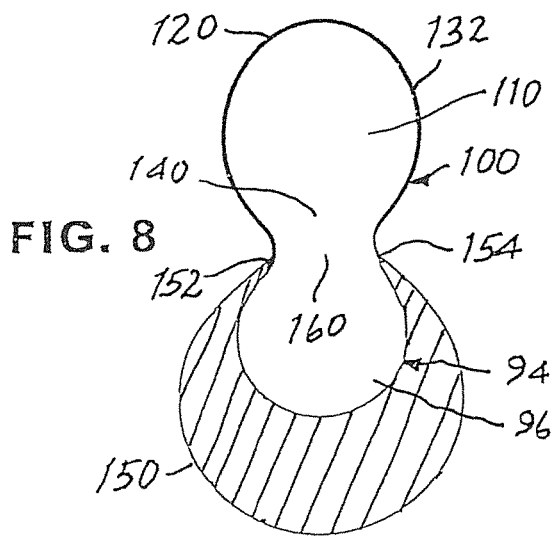
FIG. 8 is an enlarged version of reconfigured cross-sectional view E.

Once in position within the blood vessel 54 during hemodialysis, as illustrated in FIG. 4, an arterial flow is commenced, through entrance orifice 86 and into first fluid passage 82 of first lumen 80, as depicted by minus signs (−), and thence to exit 88. Then, with insertion needle 40 withdrawn, the section 60 is reconfigured, with the wall sector 120 expanded into the expanded configuration 132 placed diametrically outside the first volume 94 of the second fluid passage 92, as seen in FIGS. 5 and 6, thus rendering the section 60 configured with expanded diametric dimensions ED and providing the second lumen 90 with the second fluid passage 92 of second predetermined cross-sectional area 140, as illustrated in FIGS. 7 and 8, thereby accommodating the venous flow rate of blood being returned to the blood vessel 54 while the arterial flow rate of blood being withdrawn from the blood vessel 54 is accommodated by the first fluid passage 82 of first predetermined cross-sectional area 84 of the first lumen 80, as illustrated in FIGS. 5 and 6.

The material of a circumferential wall portion 150 of section 60 of the tubular wall 32 is sufficiently resistant to collapse, as is common in the construction of hemodialysis catheters, one such material being polyurethane. The collapse-resistant material of tubular wall 32 is continued through the circumferential wall portion 150 of section 60, between circumferentially spaced apart wall portion boundaries 152 and 154, while the material of the wall sector 120 is a flexible film-like polymeric material, such as a relatively thin polyurethane film, thin relative to circumferential wall portion 150, and integrated with and arranged relative to circumferential wall portion 150 for enabling the wall sector 120 to be folded diametrically into the folded collapsed configuration 130 for subsequent unfolding diametrically into the expanded configuration 132. In the illustrated preferred construction, wall sector 120 is integrated with circumferential wall portion 150 of section 60, between the wall portion boundaries 152 and 154, at which wall portion boundaries 152 and 153 the wall sector 120 is integrated with the material of circumferential wall portion 150, spanning a circumferential gap 160 which extends between the wall portion boundaries 152 and 154, beyond the circumferential wall portion 150. With insertion needle 40 in place, extended longitudinally through section 60 of tubular wall 32, sector 120 is folded and wrapped circumferentially around insertion needle 40, as seen in FIGS. 1 and 2, at cross-sectional views B, C, D and E, and in FIG. 3, access to insertion needle 40 being made available through gap 160 for accomplishing that end.

As seen in FIGS. 2 and 3, insertion needle 40, with the folded wall sector 120 in the collapsed configuration 130 wrapped circumferentially around insertion needle 40, is placed within second lumen 90, nested within first volume 94. In the preferred construction, the distance between wall portion boundaries 152 and 154 is less than the given diameter D of insertion needle 40, thereby precluding any inadvertent escape of insertion needle 40 from the nested position within first volume 94 by a lateral displacement through gap 160. Upon completion of full insertion of catheter 20, insertion needle 40 is withdrawn, in the conventional manner, leaving behind the folded, collapsed wall sector 120. Then, while circumferential wall portion 150 of section 60 resists collapse as blood is withdrawn from blood vessel 54 through first lumen 80 at the arterial flow rate, as depicted in FIG. 5 by minus signs (−), wall sector 120 is expanded from the folded, collapsed configuration 130, through gap 160, into the unfolded, expanded configuration 132, and remains in the expanded configuration 132 to accommodate the venous flow rate of blood returned to blood vessel 54 through the second lumen 90, as depicted in FIG. 5 by plus signs (+), by virtue of the pressure differential established between the first lumen 80 and the second lumen 90 as the arterial flow and the venous flow are continued during the hemodialysis procedure. As the arterial flow and the venous flow continue, the longitudinal spacing LS between the entrance orifice 86 and distal terminal end 36 of tubular wall 32, provided by subsection 144 extending along distal segment 72 of section 60, serves to militate against blood returned by the venous flow at distal terminal end 36 from immediately entering entrance orifice 86 as blood being withdrawn as arterial flow, commonly referred to as "recirculation".

Alternately, the wall sector 120 may be constructed of a shape-memory polymer, such as a cross-linked shape-memory polyurethane, whereby, upon insertion of section 60 into blood vessel 54, the elevated temperature and/or humidity within blood vessel 54 will induce sector 120 to return from the collapsed configuration 130 to the expanded configuration 132.

Turning now to FIGS. 9 through 14, another catheter constructed in accordance with the present invention is shown at 220 and is seen to include a tubular member 230 having a tubular wall 232 extending longitudinally from a proximal portion 234 of the tubular member 230 to a distal terminal end 236 at distal tip 238 of the tubular member 230.

Figure 11:
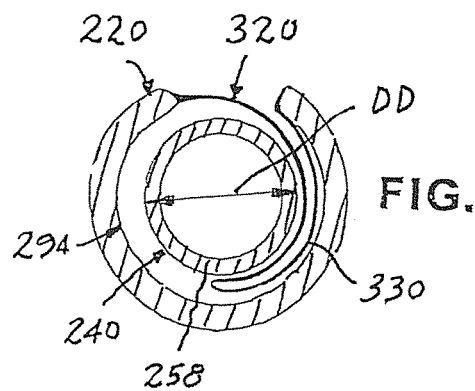
FIG. 11 is an enlarged version of cross-sectional view EE.
Figure 9:
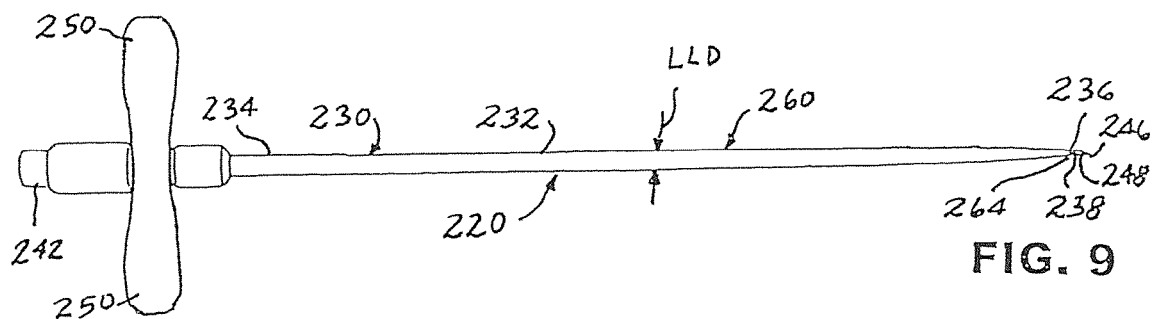
FIG. 9 is a plan view of another catheter constructed in accordance with the present invention.
Figure 10:
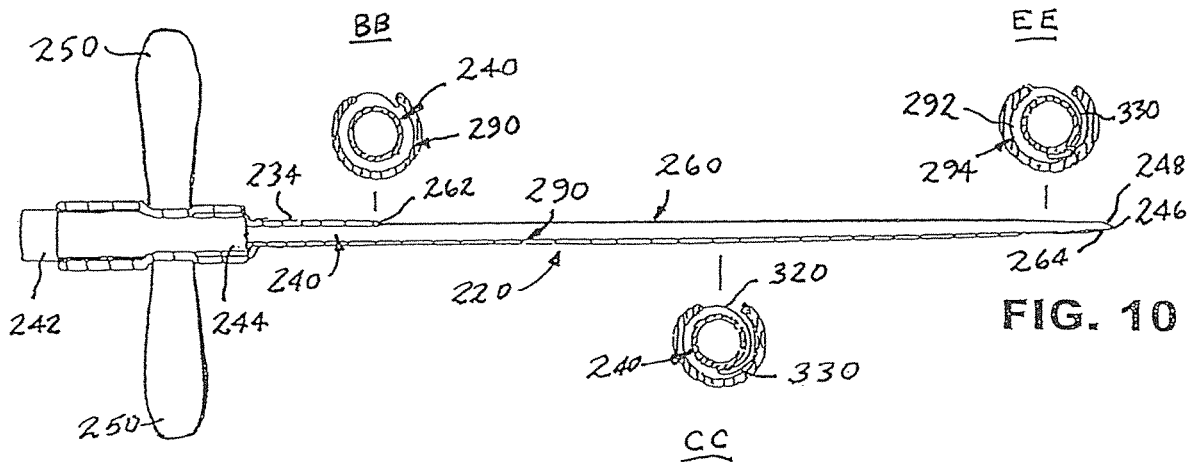
FIG. 10 is a somewhat diagrammatic view showing a longitudinal cross-section of the catheter of FIG. 9, with supplemental transverse cross-sectional views BB, CC and EE.

In preparation for insertion of catheter 220 in connection with the flow of a fluid into a blood vessel, an insertion needle 240 is placed within tubular member 230, as shown in FIGS. 9 through 11, the needle 240 including a handle 242 at the proximal end 244 of the needle 240, a piercing point 246 at the distal end 248 of the needle 240, with the piercing point 246 placed at the distal tip 238 of the tubular member 230, and a given diameter DD. A pair of wings 250 extend radially outwardly from the tubular member 230 adjacent the proximal portion 234 of tubular member 230, and provide finger grips for manipulating catheter 220 during insertion into and removal from a blood vessel 254 at an insertion site 256, both illustrated in phantom in FIG. 12, in a manner similar to that described above in connection with manipulation of hemodialysis catheter 20. Insertion needle 240 includes a central passage 258 for confirming the insertion, in the conventional manner.

The construction of catheter 220 provides a function enabling catheter 220 to be employed for accommodating a fluid flow at a required relatively high prescribed volumetric flow rate of fluid into blood vessel 254. In order to accomplish the accommodation of the required prescribed volumetric flow rate of fluid into a blood vessel, catheter 220 must be provided with a lumen having a fluid passage of predetermined cross-sectional area sufficient to accommodate the requisite prescribed volumetric flow rate. In order to accomplish a minimally invasive insertion of catheter 220 at a selected insertion site, catheter 220 is provided with limited diametric dimensions during insertion and a construction which is reconfigured, subsequent to insertion, with expanded diametric dimensions for establishing the full cross-sectional area necessary to accommodate the requisite prescribed volumetric flow rate of fluid through the lumen during the flow of fluid into a blood vessel.

Accordingly, tubular wall 232 includes a section 260 of limited diametric dimensions LLD for facilitating insertion of the section 260 into blood vessel 254 at insertion site 256, section 260 extending longitudinally between a proximal end 262, adjacent proximal portion 234 of tubular member 230, and a distal end 264 juxtaposed with the distal terminal end 236 of tubular wall 232. A lumen 290 extends longitudinally through section 260, from the proximal end 262 of the section 260 to the distal terminal end 236 of the tubular wall 232. A fluid passage 292 within lumen 290 includes a first volume 294 having a first cross-sectional area 296 and a second volume 300 having a second cross-sectional area 310, the second volume 300 extending side-by-side and contiguous with the first volume 294.

Figure 12:
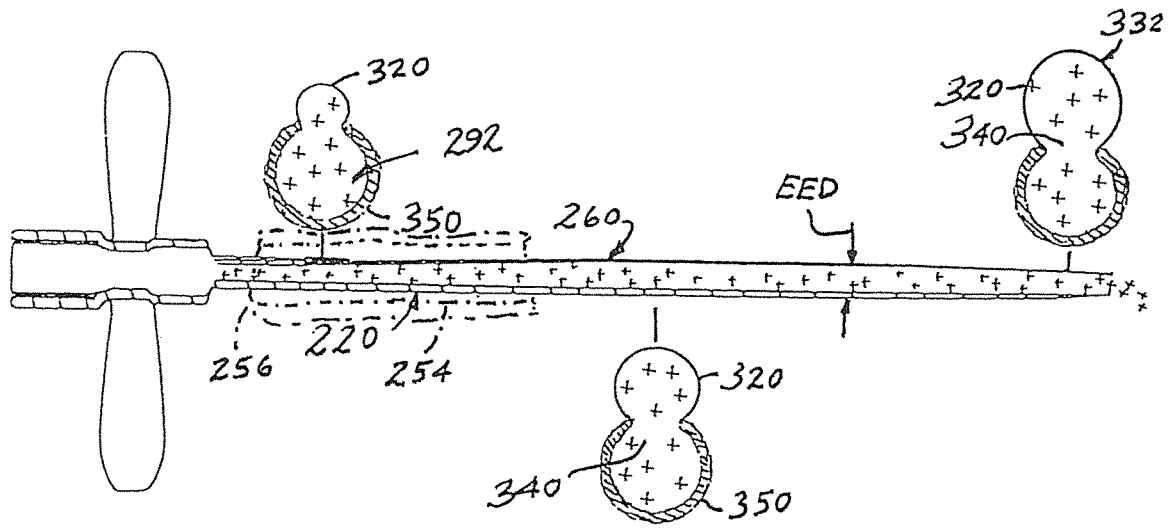
FIG. 12 is a somewhat diagrammatic view similar to FIG. 10 and showing the catheter reconfigured during a stage of operation of the catheter, subsequent to insertion.
Figure 13:
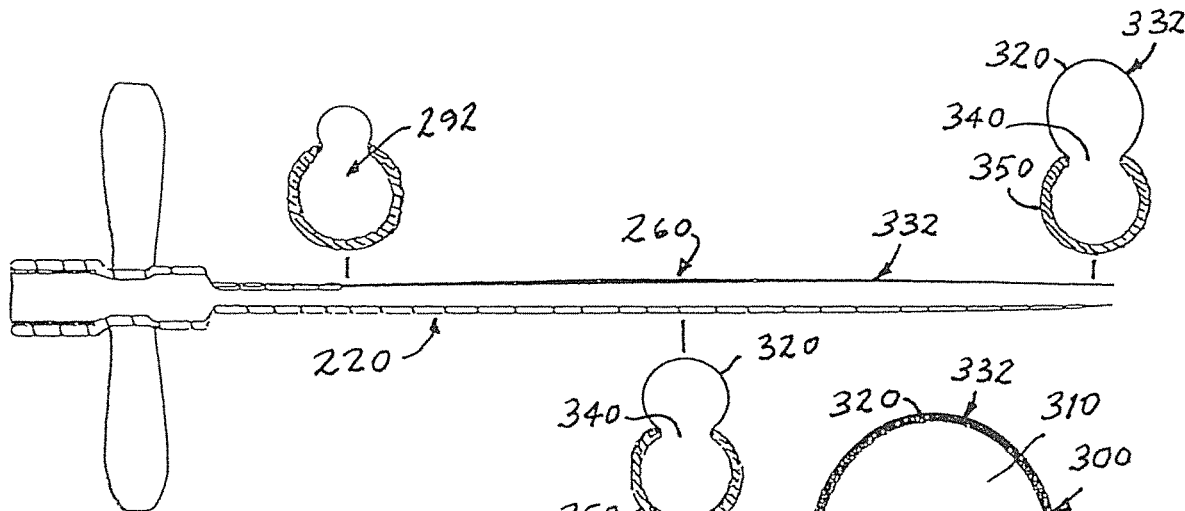
FIG. 13 is a somewhat diagrammatic view similar to FIG. 12 and illustrating the catheter itself in the reconfigured construction.

The section 260 of the tubular wall 232 is provided with a wall sector 320 having a length extending longitudinally substantially from the proximal end 262 of the section 260 to the distal terminal end 236 of the tubular wall 232, the wall sector 320 extending side-by-side and contiguous with the second volume 300 of the fluid passage 292, with the wall sector 320 bounding the second cross-sectional area 310. The wall sector 320 is constructed of a material enabling the wall sector 320 to be collapsed diametrically into a substantially collapsed configuration 330, as seen in FIG. 10 at cross-sectional views BB, CC and EE, and in FIG. 11, and to be expanded diametrically between the substantially collapsed configuration 330, wherein the wall sector 320 is configured and dimensioned for nesting within the first volume 294 of the fluid passage 292 of the section 260 of tubular wall 232, as seen in FIG. 10 at cross-sectional views BB, CC and EE, and in FIG. 11, and an expanded configuration 332, wherein the wall sector 320 is extended diametrically outside the first volume 294 of the fluid passage 292, as seen in FIGS. 12 and 13, thereby supplementing the first volume 294 having a first cross-sectional area 296 with the second volume 300 having second cross-sectional area 310 to establish, within the lumen 290, the fluid passage 292 with a second predetermined cross-sectional area 340. Thus, with the wall sector 320 in the substantially collapsed configuration 330, and nested within the first volume 294 of the fluid passage 292, as seen in FIGS. 10 and 11, the section 260 is configured with the limited diametric dimensions LLD for facilitating insertion of the section 260 into a blood vessel. Insertion is further facilitated by the presence of insertion needle 240 within tubular member 230 by virtue of the reinforcement of tubular member 230 by the presence of needle 240.

Figure 14:
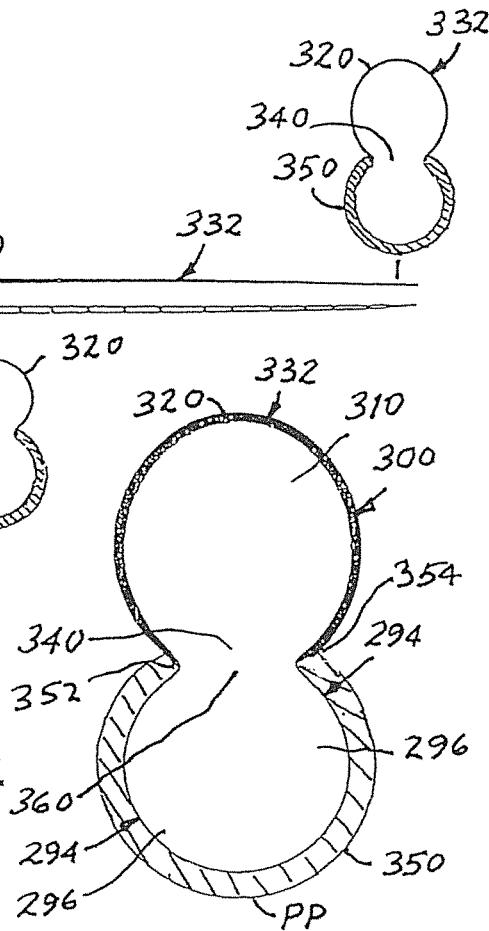
FIG. 14 is an enlarged version of cross-sectional view EE, as depicted in FIG. 13.

Once in position within blood vessel 254, with insertion needle 240 withdrawn, the section 260 is reconfigured, with the wall sector 320 expanded into the expanded configuration 332 placed diametrically outside the first volume 294 of the fluid passage 292, as seen in FIGS. 12, 13 and 14, thus rendering the section 260 configured with expanded diametric dimensions EED and providing the lumen 290 with the fluid passage 292 of second predetermined cross-sectional area 340, thereby accommodating the flow rate of fluid being flowed into blood vessel 254, as illustrated by the plus signs (+) in FIG. 12.

The material of a circumferential wall portion 350 of section 260 of the tubular wall 232 is sufficiently resistant to collapse, as is common in the construction of catheters, one such material being a suitable synthetic polymeric material such as polyurethane. The collapse-resistant material of tubular wall 232 is continued through the circumferential wall portion 350 of section 260, between circumferentially space apart wall portion boundaries 352 and 354, while the material of the wall sector 320 is a flexible film-like synthetic polymeric material, such as a relatively thin polyurethane film, thin relative to circumferential wall portion 350, integrated with and arranged relative to circumferential wall portion 350 for enabling the wall sector 322 be folded diametrically into the collapsed configuration 330 for subsequent unfolding diametrically into the expanded configuration 332. In the illustrated preferred construction, wall sector 320 is integrated with circumferential portion 350 of section 260, between the wall portion boundaries 352 and 354, at which wall portion boundaries 352 and 353 the wall sector 320 is integrated with the material of circumferential wall portion 350, spanning a circumferential gap 360 which extends between the wall portion boundaries 352 and 354, beyond the circumferential wall portion 350. With insertion needle 240 in place, extended longitudinally through section 260 of tubular wall 232, sector 320 is folded and wrapped circumferentially around insertion needle 240, as seen in FIG. 10, at cross-sectional views BB, CC, and EE, and in FIG. 11, access to insertion needle 240 being made available through gap 360 for accomplishing that end.

As seen in FIGS. 10 and 11, insertion needle 240, with the folded wall sector 320 in the collapsed configuration 330 wrapped circumferentially around insertion needle 240, is placed within lumen 290, nested within first volume 294 for operation in a manner now conventional in connection with insertion of a catheter. In the preferred construction, the distance between wall portion boundaries 352 and 354 is less than the given diameter DD of insertion needle 240, thereby precluding any inadvertent escape of insertion needle 240 from the nested position within first volume 294 by a lateral displacement through gap 360. Upon completion of full insertion of catheter 220, insertion needle 240 is withdrawn, in the conventional manner, leaving behind the folded, collapsed wall sector 320. Then, while circumferential wall portion 350 of section 260 resists collapse, wall sector 320 is expanded from the folded, collapsed configuration 330, through gap 360, into the unfolded, expanded configuration 332, and remains in the expanded configuration 332 to accommodate the flow rate of fluid passed into blood vessel 254 through the lumen 290, as depicted in FIG. 12 by plus signs (+), by virtue of the pressure within lumen 290 as the fluid flow is continued.

Alternately, the wall sector 320 may be constructed of a shape-memory polymer, such as a cross-linked shape-memory polyurethane, whereby, upon insertion of section 260 into a blood vessel, the elevated temperature and/or humidity within the blood vessel will induce sector 322 return from the collapsed configuration 330 to the expanded configuration 332.

It will be seen that the present invention attains all of the objects and advantages summarized above, namely: Enables minimally invasive percutaneous intravascular access for establishing a requisite relatively high volumetric flow rate of fluid into or out of an accessed blood vessel, while militating against the consequences of a larger opening at the access site; accomplishes a requisite high volumetric flow rate through insertion of a relatively small diameter, flexibly comfortable intravascular access tubular member, while avoiding a larger access opening at the insertion site; eliminates the need for more than one access site in a hemodialysis procedure, while reducing the size of the access opening at the single access site; reduces the size of an access opening at an insertion site, and an incursion at a blood vessel associated with the access site, without compromising a desired high volumetric rate of blood flow; increases the accuracy of placement of an inserted tubular member in attaining intravascular access; improves patient comfort and satisfaction; avoids leakage at an insertion site, with a concomitant reduction in blood loss and the risk of spreading blood-born infectious diseases from a patient to attending medical personnel, as well as others; enhances and accelerates healing at the insertion site; reduces the risk of infection; facilitates an intravascular access procedure for added effectiveness with increased ease.

it is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. A hemodialysis catheter having a construction for facilitating percutaneous intravascular access, the catheter including a first lumen and a second lumen, the first lumen having a first fluid passage of first predetermined cross-sectional area for accommodating, during the conduct of hemodialysis wherein the catheter is positioned within a blood vessel, a prescribed volumetric flow rate as an arterial flow rate of blood being withdrawn from the blood vessel, while the second lumen has a second fluid passage of second predetermined cross-sectional area corresponding to the first predetermined cross-sectional area for accommodating the prescribed volumetric flow rate as a venous flow rate of blood being returned to the blood vessel, the catheter comprising:

a tubular wall having a distal terminal end and a section of limited diametric dimensions for facilitating insertion of the section into the blood vessel, the section extending longitudinally between a proximal end and a distal end juxtaposed with the distal terminal end of the tubular wall, the section including a proximal segment and a distal segment, the proximal segment extending from the proximal end of the section to a distal end at the distal segment, and the distal segment extending from the distal end of the proximal segment to the distal terminal end of the tubular wall;

the first lumen extending longitudinally within the proximal segment, with the first fluid passage extending from an entrance orifice juxtaposed with the distal end of the proximal segment to an exit juxtaposed with the proximal end of the section;

the second lumen extending longitudinally through the section, from the proximal end of the section to the distal terminal end of the tubular wall, the second fluid passage including a first volume having a first cross-sectional area and a second volume having a second cross-sectional area, the second volume extending side-by-side and contiguous with the first volume;

a septum separating the first lumen from the second lumen;

the section of the tubular wall including a wall sector having a length extending longitudinally substantially from the proximal end of the section to the distal terminal end of the tubular wall, the wall sector extending side-by-side and contiguous with the second volume of the second fluid passage, with the wall sector bounding the second cross-sectional area; and the wall sector being constructed of a material enabling the wall sector to be collapsed diametrically into a substantially collapsed configuration and to be expanded diametrically between the substantially collapsed configuration, wherein the wall sector is configured and dimensioned for nesting internally inside the first volume of the second fluid passage of the section of the tubular wall, and an expanded configuration wherein the wall sector is extended diametrically outside the first volume of the second fluid passage, thereby supplementing the first volume of first cross-sectional area with the second volume of second cross-sectional area to establish, within the second lumen, the second fluid passage of second predetermined cross-sectional area corresponding to the predetermined cross-sectional area of the first lumen;

whereby, when the wall sector is in the substantially collapsed configuration, the wall sector is nested internally inside the first volume of the second fluid passage and the section is provided with the limited diametric dimensions that facilitate insertion of the segment into the blood vessel and, when positioned within the blood vessel during hemodialysis, the wall sector is in the expanded configuration, placed diametrically outside the first volume of the second fluid passage, such that the section is provided with expanded diametric dimensions and the second lumen is provided with the second fluid passage of second predetermined cross-sectional area for accommodating the venous flow rate of blood being returned to the blood vessel, while the arterial flow rate of blood being withdrawn from the blood vessel is accommodated by the first fluid passage of first predetermined cross-sectional area of the first lumen.

2. The hemodialysis catheter of claim 1 wherein the material of the wall sector is a flexible, film-like polymeric material extending longitudinally and folded diametrically into the collapsed configuration for subsequent unfolding diametrically into the expanded configuration.

3. The hemodialysis catheter of claim 1 wherein the material of the wall sector is a shape-memory polymer.

4. The hemodialysis catheter of claim 1 wherein the tubular wall includes a reinforcing subsection extending longitudinally along the distal segment, diametrically opposite the wall sector, the subsection providing a longitudinal length between the entrance orifice and the distal terminal end of the tubular wall for militating against the immediate withdrawal through the entrance orifice of blood returned at the terminal end of the tubular wall.

5. The hemodialysis catheter of claim 1 wherein during insertion of the catheter into the blood vessel, the collapsed configuration of the wall sector is arranged wrapped circumferentially around an insertion needle extending longitudinally through the section of the tubular wall, within the second lumen.

6. The hemodialysis catheter of claim 5 wherein, the section of the tubular wall includes a circumferential wall portion extending contiguous with the first volume, between circumferentially spaced apart wall portion boundaries, and a circumferential gap extending between the circumferentially spaced apart wall portion boundaries, the wall sector being integrated with the circumferential wall portion at the wall portion boundaries and spanning the circumferential gap.

7. The hemodialysis catheter of claim 6 wherein the insertion needle has a given diameter, and the circumferential gap extends along a distance between the wall portion boundaries less than the given diameter of the insertion needle.

8. A catheter having a construction for facilitating percutaneous intravascular access, the construction providing the catheter with a lumen having a fluid passage of predetermined cross-sectional area for accommodating, upon insertion into a blood vessel, a prescribed volumetric flow rate of fluid through the catheter, the catheter comprising:

a tubular wall having a distal terminal end and a section of limited diametric dimensions for facilitating insertion of the section into the blood vessel, the section extending longitudinally between a proximal end and the distal terminal end of the tubular wall;

the lumen extending longitudinally through the section, from the proximal end of the section to the distal terminal end of the section, the fluid passage including a first volume having a first cross-sectional area, and a second volume having a second cross-sectional area, the second volume extending side-by-side and contiguous with the first volume;

the section of the tubular wall including a wall sector having a length extending longitudinally substantially from the proximal end of the section to the distal terminal end of the tubular wall, the wall sector extending side-by-side and contiguous with the second volume of the fluid passage, with the wall sector bounding the second cross-sectional area; and the wall sector being constructed of a material enabling the wall sector to be collapsed diametrically into a substantially collapsed configuration and to be expanded diametrically between the substantially collapsed configuration, wherein the wall sector is configured and dimensioned for nesting internally inside the first volume of the fluid passage, and an expanded configuration wherein the wall sector is extended diametrically outside the first volume, thereby supplementing the first volume of first cross-sectional area with the second volume of second cross-sectional area to establish, within the section, the fluid passage of predetermined cross-sectional area;

whereby, when the wall sector is in the substantially collapsed configuration, the wall sector is nested internally inside the first volume, the section is provided with the limited diametric dimensions that facilitate insertion of the section into the blood vessel and, when positioned within the blood vessel, the wall sector is in the diametrically expanded configuration, placed diametrically outside the first volume, such that the section is provided with expanded diametric dimensions and the lumen is provided with the fluid passage of predetermined cross-sectional area for accommodating the prescribed volumetric flow rate of fluid through the catheter.

9. The catheter of claim 8 wherein the material of the wall sector is a flexible, film-like polymeric material extending longitudinally and folded diametrically into the collapsed configuration for unfolding diametrically into the expanded configuration.

10. The catheter of claim 8 wherein the material of the wall sector is a shape-memory polymer.

11. The catheter of claim 8 wherein during insertion of the catheter into the blood vessel, the collapsed configuration of the wall sector is arranged wrapped circumferentially around an insertion needle extending longitudinally through the section of the tubular wall, within the second volume.

12. The catheter of claim 11 wherein, the section of the tubular wall includes a circumferential wall portion contiguous with the first volume, between circumferentially spaced apart wall portion boundaries, and a circumferential gap extending between the circumferentially spaced apart wall portion boundaries, the wall sector being integrated with the circumferential wall portion at the wall portion boundaries and spanning the circumferential gap.

13. The catheter of claim 12 wherein the insertion needle has a given diameter, and the circumferential gap extends along a distance between the wall portion boundaries less than the given diameter of the insertion needle.

14. A method for facilitating percutaneous intravascular access by a hemodialysis catheter, the catheter including a first lumen and a second lumen, the first lumen having a first fluid passage of first predetermined cross-sectional area for accommodating, during the conduct of a hemodialysis procedure wherein the catheter is positioned within a blood vessel, a prescribed volumetric flow rate as an arterial flow rate of blood being withdrawn from the blood vessel, while the second lumen has a second fluid passage of second predetermined cross-sectional area corresponding to the first predetermined cross-sectional area for accommodating the prescribed volumetric flow rate as a venous flow rate of blood being returned to the blood vessel, the method comprising:
  providing the catheter with a tubular wall having a distal terminal end and a section of limited diametric dimensions for facilitating insertion of the section into the blood vessel;
  extending the section longitudinally between a proximal end and a distal end juxtaposed with the distal terminal end of the tubular wall;
  including in the section a proximal segment and a distal segment, with the proximal segment extending from the proximal end of the section to a distal end at the distal segment, and the distal segment extending from the distal end of the proximal segment to the distal terminal end of the tubular wall;
  extending the first lumen longitudinally within the proximal segment, with the first fluid passage extending from an entrance orifice juxtaposed with the distal end of the proximal segment to an exit juxtaposed with the proximal end of the section;
  extending the second lumen longitudinally through the section, from the proximal end of the section to the distal terminal end of the tubular wall;
  including in the second fluid passage a first volume having a first cross-sectional area and a second volume having a second cross-sectional area, the second volume extending side-by-side and contiguous with the first volume;
  separating the first lumen from the second lumen;
  including in the section of the tubular wall a wall sector having a length extending longitudinally substantially from the proximal end of the section to the distal terminal end of the tubular wall, the wall sector extending side-by-side and contiguous with the second volume of the second fluid passage, with the wall sector bounding the second cross-sectional area; and
  constructing the wall sector of a material enabling the wall sector to be collapsed diametrically into a substantially collapsed configuration and to be expanded diametrically between the substantially collapsed configuration, wherein the wall sector is configured and dimensioned for nesting internally inside the first volume of the second fluid passage of the section of the tubular wall, and an expanded configuration wherein the wall sector is to extend diametrically outside the first volume of the second fluid passage, thereby supplementing the first volume of first cross-sectional area with the second volume of second cross-sectional area to establish, within the second lumen, the second fluid passage of second predetermined cross-sectional area corresponding to the predetermined cross-sectional area of the first lumen;
  whereby, with the wall sector in the substantially collapsed configuration and nested internally inside the first volume of the second fluid passage, the section is configured with the limited diametric dimensions for facilitating insertion of the segment into the blood vessel and, upon being positioned within the blood vessel during hemodialysis, the section is reconfigured with the wall sector expanded into the expanded configuration, placed diametrically outside the first volume of the second fluid passage, thereby rendering the section configured with expanded diametric dimensions and providing the second lumen with the second fluid passage of second predetermined cross-sectional area, for accommodating the venous flow rate of blood being returned to the blood vessel, while the arterial flow rate of blood being withdrawn from the blood vessel is accommodated by the first fluid passage of first predetermined cross-sectional area of the first lumen.

15. The method of claim 14 including constructing the wall sector of a flexible, film-like polymeric material, and folding the wall sector diametrically into the collapsed configuration for subsequent unfolding diametrically into the expanded configuration.

16. The method of claim 14 including constructing the wall sector of a thermally induced shape-memory polymer.

17. The method of claim 14 including, prior to insertion of the catheter into the blood vessel, placing an insertion needle longitudinally through the section of the tubular wall, within the second volume, and wrapping the wall sector circumferentially around the insertion needle.

18. The method of claim 17 including providing the section of the tubular wall with a circumferential wall portion contiguous with the first volume, extending the circumferential wall portion between circumferentially spaced apart wall portion boundaries, and extending a circumferential gap between the circumferentially spaced apart wall portion boundaries, beyond the circumferential wall portion, and integrating the wall sector with the circumferential wall portion at the wall portion boundaries, with the wall sector spanning the circumferential gap.

19. The method of claim 18 including providing the insertion needle with a given diameter, and extending the circumferential gap along a distance between the wall portion boundaries less than the given diameter of the insertion needle.

20. A method for facilitating percutaneous intravascular access by a catheter, the method comprising:
  providing the catheter with a tubular wall having a distal terminal end and a section of limited diametric dimensions;
  extending the section longitudinally between a proximal end and the distal terminal end of the tubular wall;
  extending a lumen longitudinally through the section, from the proximal end of the section to the distal terminal end of the section;
  providing the lumen with a fluid passage including a first volume having a first cross-sectional area, and a second volume having a second cross-sectional area, with the second volume extending side-by-side and contiguous with the first volume;
  including in the section of the tubular wall, a wall sector having a length extending longitudinally substantially from the proximal end of the section to the distal terminal end of the tubular wall, with the wall sector extending side-by-side and contiguous with the second volume of the fluid passage, with the wall sector bounding the second cross-sectional area; and constructing the wall sector of a material enabling the wall sector to be collapsed diametrically into a substantially collapsed configuration and to be expanded diametrically between the substantially collapsed configuration, wherein the wall sector is configured and dimensioned for nesting internally inside the first volume of the fluid passage, and an expanded configuration wherein the wall sector is to extend diametrically outside the first volume, thereby supplementing the first volume of first cross-sectional area with the second volume of second cross-sectional area to establish, within the section, the fluid passage of predetermined cross-sectional area;

whereby, with the wall sector in the substantially collapsed configuration and nested internally inside the first volume, the section is configured with the limited diametric dimensions for facilitating insertion of the section into a blood vessel and, upon being positioned within the blood vessel, the section is reconfigured with the wall sector expanded into the expanded configuration, placed diametrically outside the first volume, thereby rendering the section configured with expanded diametric dimensions and providing the lumen with the fluid passage of predetermined cross-sectional area for accommodating the prescribed volumetric flow rate of fluid through the catheter.

21. The method of claim 20 including constructing the wall sector of a flexible, film-like polymeric material, and folding the wall sector diametrically into the collapsed configuration for subsequent unfolding diametrically into the expanded configuration upon insertion of the catheter into the blood vessel.

22. The method of claim 20 including constructing the wall sector of a shape-memory polymer.

23. The method of claim 20 including, prior to insertion of the catheter into the blood vessel, wrapping the wall sector circumferentially around an insertion needle, and placing the insertion needle, with the wrapped wall sector, longitudinally through the section of the tubular wall, within the second volume.

24. The method of claim 23 including providing the section of the tubular wall with a circumferential wall portion contiguous with the first volume, extending the circumferential wall portion between circumferentially spaced apart wall portion boundaries, extending a circumferential gap between the circumferentially spaced apart wall portion boundaries, beyond the circumferential wall portion, and integrating the wall sector with the circumferential wall portion at the wall portion boundaries, with the wall sector spanning the circumferential gap.

25. The method of claim 24 including providing the insertion needle with a given diameter, and extending the circumferential gap along a distance between the wall portion boundaries less than the given diameter of the insertion needle.

* * * * *